US011118155B2

(12) United States Patent
Lee

(10) Patent No.: US 11,118,155 B2
(45) Date of Patent: Sep. 14, 2021

(54) INTERCELLULAR SEPARATION METHOD FOR CULTURED CELLS

(71) Applicant: MEDIKAN INC., Seoul (KR)

(72) Inventor: Hee Young Lee, Seoul (KR)

(73) Assignee: MEDIKAN INC., Seoul (KR)

(*) Notice: Subject to any disclaimer, the term of this patent is extended or adjusted under 35 U.S.C. 154(b) by 257 days.

(21) Appl. No.: 15/559,016

(22) PCT Filed: Apr. 5, 2016

(86) PCT No.: PCT/KR2016/003489
§ 371 (c)(1),
(2) Date: Sep. 15, 2017

(87) PCT Pub. No.: WO2016/163704
PCT Pub. Date: Oct. 13, 2016

(65) Prior Publication Data
US 2018/0080003 A1    Mar. 22, 2018

(30) Foreign Application Priority Data

Apr. 6, 2015    (KR) .......................... 10-2015-0048247

(51) Int. Cl.
*C12M 1/00*    (2006.01)
*C12M 1/12*    (2006.01)
(Continued)

(52) U.S. Cl.
CPC ................ *C12N 1/02* (2013.01); *C12M 1/12* (2013.01); *C12M 29/04* (2013.01); *C12M 33/04* (2013.01);
(Continued)

(58) Field of Classification Search
CPC ........ C12N 1/02; C12N 5/00; C12N 2509/10; C12M 47/04; C12M 47/02; C12M 1/12;
(Continued)

(56) References Cited

U.S. PATENT DOCUMENTS

2007/0298451 A1*  12/2007  Ribault ................... C12Q 1/24
                                                                      435/30
2011/0318814 A1*  12/2011  Kshirsagar ............. C12M 47/04
                                                                      435/239
(Continued)

FOREIGN PATENT DOCUMENTS

KR    1020140099516    8/2014

*Primary Examiner* — Lucas A Stelling
(74) *Attorney, Agent, or Firm* — Weiss & Moy, P.C.; Jeffrey D. Moy

(57) ABSTRACT

The present invention relates to a method of separating cultured cells, which is used in a configuration including: a first accommodation space; a cell suspension which is present in a liquid in the first accommodation space in a state in which a plurality of cells is connected to one another; a filter container which is hermetically connected to the first accommodation space and mounted with a cell dividing member having one or more through holes having an average diameter of 5 μm to 300 μm; and a second accommodation space which is hermetically connected to the filter container, in which the cell suspension flows from the first accommodation space to the second accommodation space through the filter, such that the connection between the cells is passively and mechanically separated while the cells collide with a fixed resistance portion of the filter.

12 Claims, 4 Drawing Sheets

(51) Int. Cl.
*C12M 1/26* (2006.01)
*C12M 1/42* (2006.01)
*C12N 1/02* (2006.01)
*C12N 5/00* (2006.01)
*C12Q 1/24* (2006.01)
*G01N 1/28* (2006.01)
*G01N 1/40* (2006.01)
*G01N 33/18* (2006.01)

(52) U.S. Cl.
CPC ............ *C12M 33/12* (2013.01); *C12M 33/14* (2013.01); *C12M 47/02* (2013.01); *C12M 47/04* (2013.01); *C12M 47/08* (2013.01); *C12N 5/00* (2013.01); *C12Q 1/24* (2013.01); *G01N 1/286* (2013.01); *C12M 1/123* (2013.01); *C12M 35/04* (2013.01); *C12M 47/06* (2013.01); *C12N 2509/10* (2013.01); *G01N 33/1866* (2013.01); *G01N 2001/4088* (2013.01)

(58) Field of Classification Search
CPC ...... C12M 47/06; C12M 33/04; C12M 33/12; C12M 33/14; C12M 47/08; C12M 29/04; C12M 35/04; C12M 1/123; C12Q 1/24; G01N 1/286; G01N 2001/4088; G01N 33/1866

See application file for complete search history.

(56) References Cited

U.S. PATENT DOCUMENTS

2014/0231335 A1\* 8/2014 Kim .................... A61M 1/3693
 210/335
2014/0356939 A1\* 12/2014 Sugiura .................. C12M 47/02
 435/297.1

\* cited by examiner

[Fig.1]
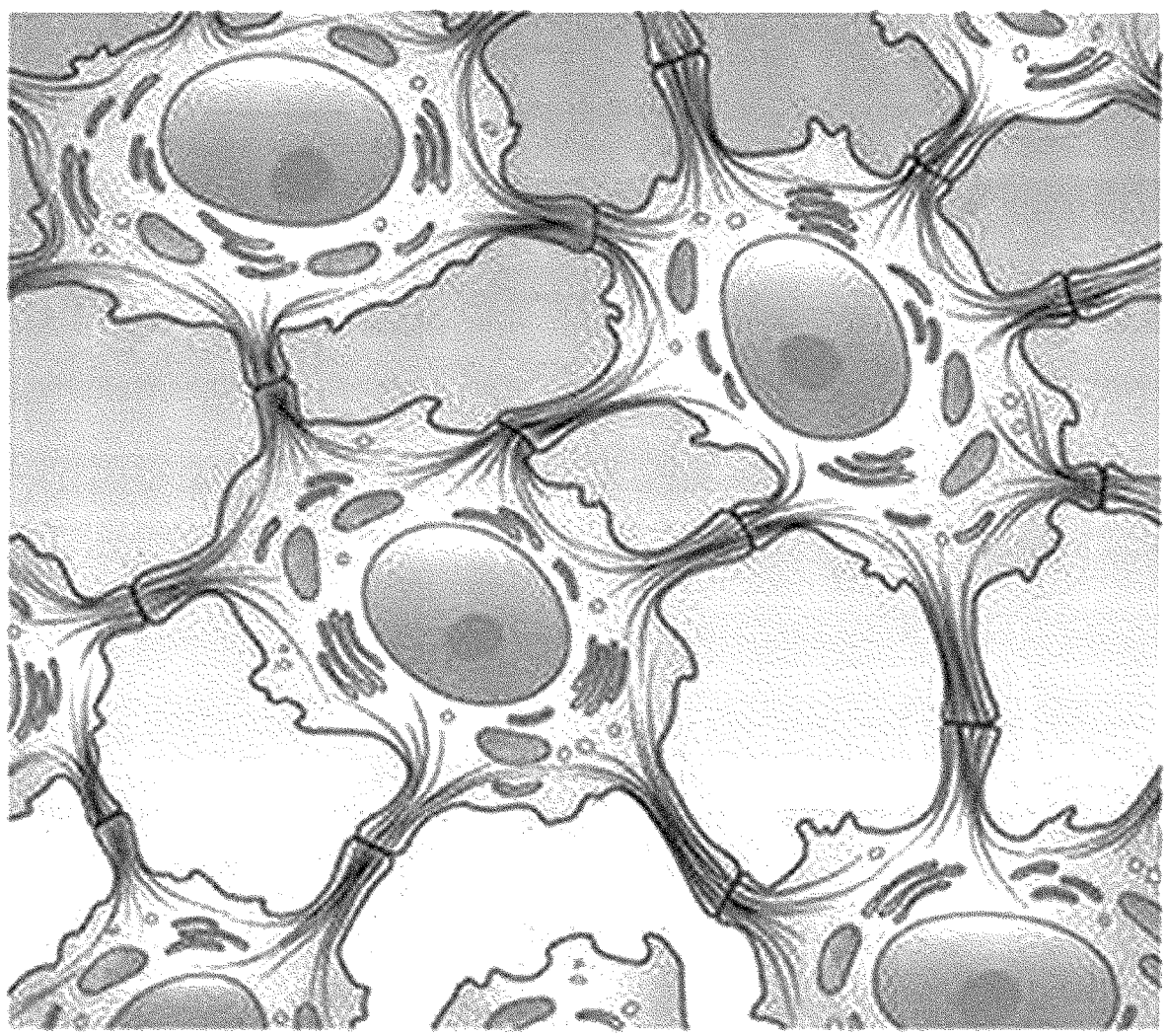

[Fig.2]
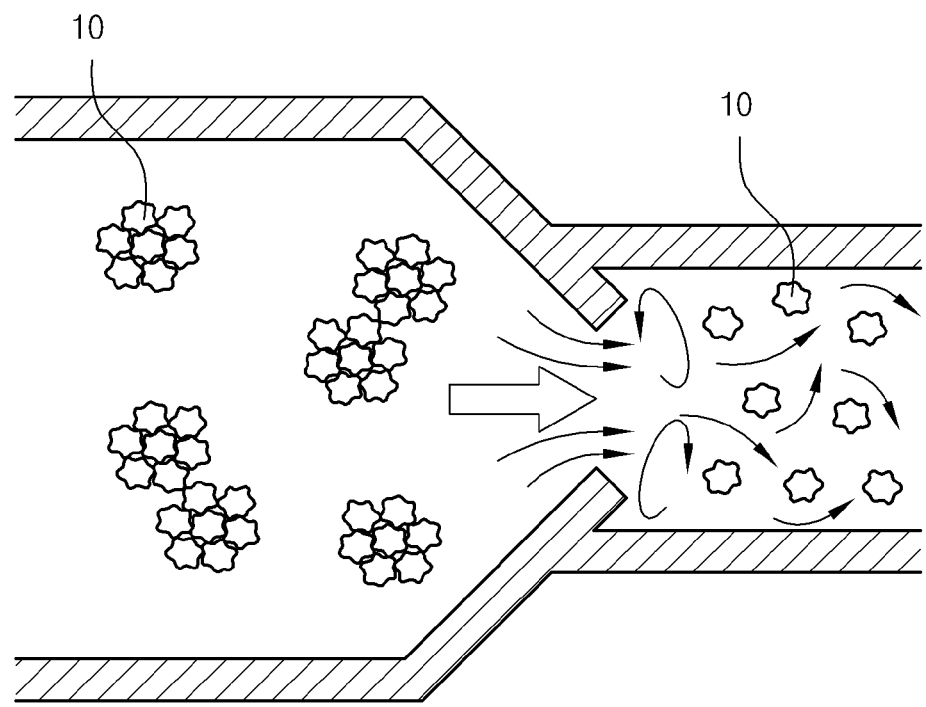

[Fig.3]
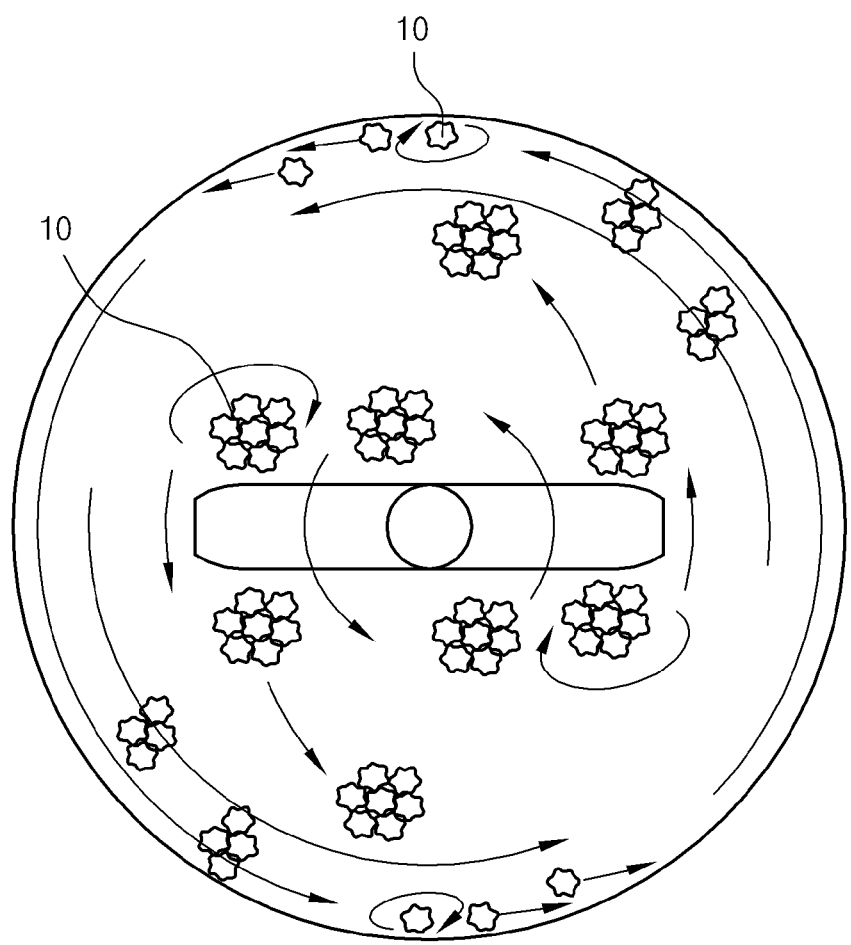

[Fig.4]
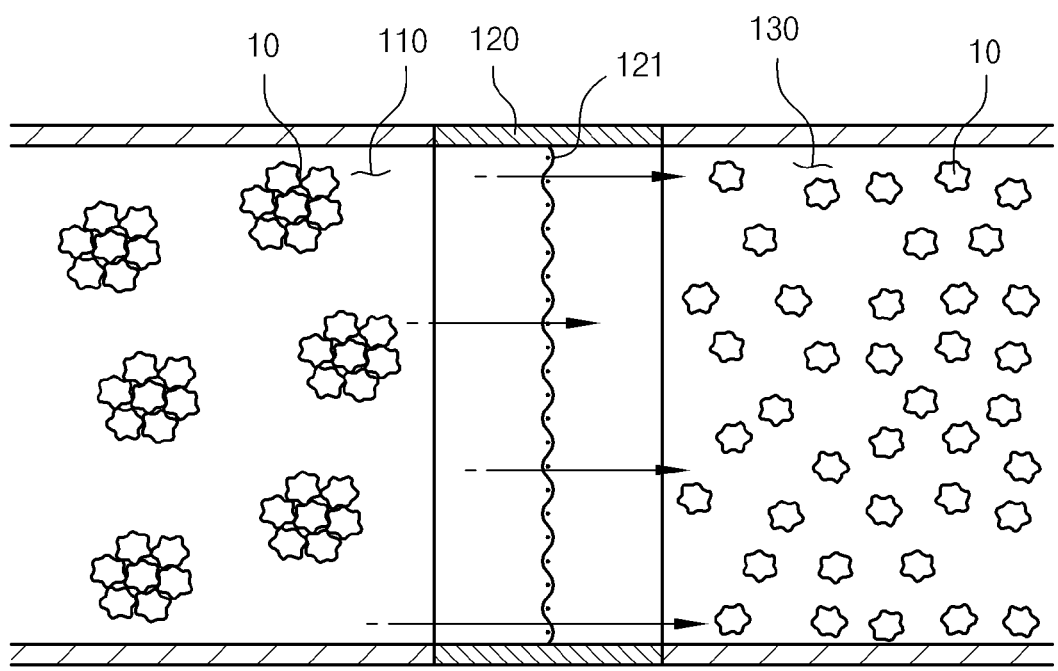

INTERCELLULAR SEPARATION METHOD FOR CULTURED CELLS

TECHNICAL FIELD

The present invention relates to a method of separating cultured cells, and more particularly, to a method of separating cells obtained from cell culture by using a water flow.

BACKGROUND ART

In some instances, animal cells such as desmosomes are strongly bonded together during cell culture. In the bond between the cells, the cells begin to be bonded together as a protrusion such as a pseudopodium is grown from cytoplasm and bonded to a protrusion of an opponent cell, and bonding strength is gradually increased.

Methods of separating the bonded cells in the related art will be described below.

First, there is a method of removing the cytoplasm protrusion by using a protein solubilizing agent such as trypsin. However, this method has a drawback in that surface properties of the cells are removed due to high cytotoxicity.

Second, there is a method of separating the cells by using shearing force of water by placing the cells into a turbulent flow of water. However, this method needs to impart maximized diversity to the turbulent flow of water or cause friction in a state in which a flow velocity is high until the cell of about 10 µm has inertia mass in different directions by using shearing force of pure water. In addition, there are problems in that it is difficult to implement the method because a boundary between laminated water flows needs to be configured by a micro fluid of 10 µm, and a process needs to be repeated several times if a difference between the flow velocities is not great. For this reason, there are problems in that a probability of damage to the cell is increased, and a separation rate is extremely low.

In addition, there is also a method of using a water flow to separate cells.

FIGS. 2 and 3 illustrate schematic views of a method of separating cells by using a water flow in the related art.

In a first method of using the water flow in the related art, the cells are moved in a group in a central high-speed movement section, and the separation occurs in the same direction on a resistance surface due to a velocity difference (see FIG. 2).

This method is inefficient in that there is no member for separating the water flows in the manner in which the cells are moved at a high flow velocity, and the separation depends only on the resistance caused by an inner wall of a tube through which the cells pass, such that there is a problem in that any separation of the cells does not occur in a flow in the central tube at a high flow velocity, but there is an attempt to overcome this problem just by repeating the process several times. This method is also inefficient in that different resistance is used outside the group of cells to allow a resistive material placed between the cells to effectively cut a connection between the cells when the group of cells flows.

A second method of using a water flow in the related art is a method of generating a turbulent flow in a cylindrical container such as a water tub (see FIG. 3).

This method is inefficient in that because a stable laminar flow is formed at a wall of the water tub, the cells are only rotated and there is no great velocity difference between the cells at the wall of the water tub. Unnecessary force is applied to the cell separated at a turbulent flow, or it is difficult to allow the cells to abut with equal probability. In addition, there is a problem in that there is a great deviation in respect to the number of times that the turbulent flow is applied. In a case in which various types of resistive materials are rotated in a rotating water flow, this case is more efficient in that intended resistance is generated, but there is a problem in that it is difficult to make a treatment probability for each cell uniform because there is no single direction water flow to which a treatment probability of a sample is uniformly applied.

To appropriately grind and mix liquid phase samples, it is necessary to treat some of the samples while allowing some of the samples to flow, collect the samples, which has been treated once, to other side of a treatment apparatus, and place the pre-treated samples and the post-treated samples in separated spaces, similar to a line mixer, a homo mixer, or the like.

As described above, it is necessary to minimize damage to the cell by minimizing external resistance applied to the cell when separating cultured cells.

DISCLOSURE

Technical Problem

To solve the aforementioned problem, an object of the present invention is to provide a method of separating cultured cells while minimizing damage to the cell.

Another object of the present invention is to provide a method which is simple and capable of separating stem cells while minimizing damage to the cell caused by external impact.

Technical Solution

To achieve the aforementioned objects, the present invention provides a method of separating cultured cells, which is used in a configuration including: a first accommodation space; a cell suspension which is present in a liquid in the first accommodation space in a state in which a plurality of cells is connected to one another; a filter container which is hermetically connected to the first accommodation space and mounted with a cell dividing member having one or more through holes having an average diameter of 5 µm to 300 µm; and a second accommodation space which is hermetically connected to the filter container, in which the cell suspension flows from the first accommodation space to the second accommodation space through the filter, such that the connection between the cells is passively and mechanically separated while the cells collide with a fixed resistance portion of the filter.

In addition, the present invention provides the method of separating cultured cells including a process of moving the cell suspension from the second accommodation space back to the first accommodation space one or more times so as to allow the cell suspension to pass through the cell dividing member several times.

The present invention provides the method of separating cultured cells, in which a plurality of cell dividing members is formed in the filter container in order to allow the cell suspension to pass through the cell dividing member several times.

The present invention provides the method of separating cultured cells, in which a second filter container is added to allow the cell suspension to pass through the cell dividing member several times, and a third accommodation space is formed to be hermetically connected to the second filter container.

The present invention provides the method of separating cultured cells, in which one or more of a woven mesh shape, a punched plate shape, and a multi-blade (radiator, gill) shape are used for the cell dividing member.

The present invention provides the method of separating cultured cells, in which the filter container is a container of which the capacity is adjustable.

The present invention provides the method of separating cultured cells, in which the filter container includes a tube through which the cell suspension is moved by being pressed.

Advantageous Effects

The method of separating cells according to the present invention has an effect of separating cultured cells while minimizing damage to the cell.

The method of separating cells according to the present invention is simple in separating the cultured cells and may separate the cells while minimizing external impact.

DESCRIPTION OF DRAWINGS

FIG. 1 is a view illustrating bond between cells in a cultured state.

FIGS. 2 and 3 illustrate schematic views of a method of separating cells by using a water flow in the related art.

FIG. 4 illustrates a schematic view of a cell separation according to an exemplary embodiment of the present invention.

DESCRIPTION OF MAIN REFERENCE NUMERALS OF DRAWINGS

10: cultured cells
110: first accommodation space
120: filter container
121: cell dividing member
130: second accommodation space

BEST MODE

Hereinafter, the present invention will be described in detail with reference to the accompanying drawings. First, it should be noted that in the drawings, like constituent elements or components are referred by like reference numerals if possible. In the description of the present invention, the specific descriptions of publicly known related function or configurations will be omitted in order to prevent the specific descriptions from obscuring the subject matter of the present invention.

Words of degree, such as "about", "substantially", and the like are used in the present specification in the sense of "at, or nearly at, when given the manufacturing, design, and material tolerances inherent in the stated circumstances" and are used to prevent the infringer from taking advantage of the invention disclosure where exact or absolute figures and operational or structural relationships are stated as an aid to understanding the invention.

A "water flow" described in the present specification refers to a state in which a liquid containing a cell culture solution flows in an accommodation space.

The present invention provides a method of separating cultured cells, which is used in a configuration including: a first accommodation space; a cell suspension which is present in a liquid in the first accommodation space in a state in which a plurality of cells is connected to one another; a filter container which is hermetically connected to the first accommodation space and mounted with a cell dividing member having one or more through holes having an average diameter of 5 μm to 300 μm; and a second accommodation space which is hermetically connected to the filter container, in which the cell suspension flows from the first accommodation space to the second accommodation space through the filter, such that the connection between the cells is passively and mechanically separated while the cells collide with a fixed resistance portion of the filter.

FIG. 4 illustrates a schematic view of a cell separation according to an exemplary embodiment of the present invention.

The present invention relates to a method of separating cultured cells in a cultured state, and more particularly, the present invention is configured such that a cell suspension, which is included in a water flow in the same direction and includes cultured cells 10 connected to one another, generates frictional resistance in a direction in which the cells are moved away from one another while passing through a cell dividing member 121 which is a solid and is fixedly positioned perpendicular to a water flow direction.

That is, the water flows are minutely divided naturally in a space in which the plurality of cell dividing members 121, which is a resistance blade operated passively, is disposed, but the directions of the water flows are basically identical to each other, such that only minimum friction required to move the cells away from one another is generated, and as a result, the cell separation is enabled while using the water flow and minimizing damage to the cell.

The method of separating the cultured cells according to the present invention is a method of removing a coupling portion between the cells in the cell culture solution including the cultured cells in a predetermined accommodation space while rarely generating great friction or a turbulent flow. The cultured cells 10 are coupled to one another in a manner in which a protrusion such as a pseudopodium is grown from cytoplasm and coupled to a protrusion of another cell. Therefore, the cell separation occurs as the coupled protrusions are disconnected by slight external impact.

To separate the cultured cells 10, the separation between the coupled cells may be naturally induced by generating a flow of the cell culture solution including the cells in the accommodation space and forming the cell dividing member 121 perpendicular to the flow direction in order to generate resistance at an intermediate portion.

The method of separating cultured cells according to the exemplary embodiment of the present invention, which is used in a configuration including: a first accommodation space 110; a cell suspension which is present in a liquid in the first accommodation space 110 in a state in which a plurality of cells is connected to one another; a filter container 120 which is hermetically connected to the first accommodation space 110 and mounted with a cell dividing member 121 having a plurality of through holes of 5 μm to 300 μm; and a second accommodation space 130 which is hermetically connected to the filter container 120, in which the cell suspension flows from the first accommodation space 110 to the second accommodation space 130 through the cell dividing member 121, such that the connection between the cells is passively and mechanically separated while the cells collide with the cell dividing member 121.

In the present invention, to separate the cultured cells, there may be the first accommodation space 110, the filter container 120 which is hermetically connected to the first accommodation space 110 and mounted with the dividing member having the plurality of through holes, and the second accommodation space 130 which is hermetically connected to the filter container 120.

The first accommodation space 110 is a space that may accommodate the cultured cells, and the cell culture solution is inputted into the first accommodation space 110, and a water flow may be generated in the first accommodation space 110. The cell culture solution is accommodated in the first accommodation space 110, and the cell culture solution may be moved by generating the water flow of the cell culture solution by external force.

The water flow, which allows the cell culture solution to flow in a predetermined direction, is uniform in velocity in the entire space, such that a turbulent flow or the like is not generated while the cell culture solution flows. To this end, the first accommodation space 110, the filter container 120, and the second accommodation space 130 may have a uniform cross-sectional area.

In addition, the first accommodation space 110 is not particularly limited, but the first accommodation space 110 may have a uniform cross-sectional area so that the water flow is constant.

The cell dividing member 121 serves to separate the cultured cells 10 in the cell culture solution flowing in the first accommodation space 110, and frictional resistance is generated when the cell culture solution flows to the space in which the plurality of dividing members, which is passively operated, is disposed, such that the cultured cells 10 are naturally divided.

The cell dividing member 121 has the through holes of 5 to 300 μm, such that when the cultured cells 10 move from the first accommodation space 110 to the second accommodation space 130, the cells are divided through the through hole.

One of the advantages of the present invention is that a turbulent flow is rarely generated. Because of the uniform cross-sectional area, the occurrence of the turbulent flow is minimized when the cell culture solution is moved in the first accommodation space 110, the filter container 120, and the second accommodation space 130, and as a result, it is possible to minimize damage to the cell caused by external impact.

In addition, the cell dividing member 121 may be formed in a mesh shape, such that a lot of through holes may be formed. The cell dividing member 121 may have one or more shapes selected from a group consisting of a punched plate shape, a multi-blade shape, and the like in addition to the mesh shape.

Meanwhile, the cell culture solution may pass through the cell dividing member 121 repeatedly several times. To this end, the process may be repeated several times such that the cell culture solution, which has been moved to the second accommodation space 130, may be moved back to the first accommodation space 110 and may pass through the cell dividing member 121.

Alternatively, the cell dividing member 121 may be formed at an end portion of the second accommodation space 130, the filter container 120 mounted with the cell dividing member 121 may be additionally formed, and the third accommodation space may be formed. Since the cell dividing member 121 is formed between the second accommodation space 130 and the third accommodation space, the cell separation may be more easily performed.

Alternatively, two or more cell dividing members 121 may be selectively formed in the filter container 120, such that the cell separation is performed several times.

In addition, the filter container 120 may be a sealed container of which the capacity is adjustable. An example of the sealed container may include a medical syringe. The medical syringe is a container sealed from the outside, the cells are moved through an injection needle, and an injection portion of the injection needle may serve as the cell dividing member 121.

In addition, the filter container 120 may be a tube through which the cell culture solution may be moved by being pressed. The tube through which the cell culture solution may be moved by being pressed may be a pump. The cultured cells 10 may be forcibly moved by applying pressure from the outside by using a device such as the pump, and the cell dividing member 121 is formed in the tube, such that the cells may be separated through the tube when the cultured cells 10 are moved by an operation of the pump.

Meanwhile, the cultured cells used in the present invention are grown on an inner surface of an incubator, and it is necessary to scrape the grown cultured cells 10 by applying external force to collect the cultured cells 10. That is, the cultured cells 10 may be used in a state in which the cultured cells 10 are scraped and agglomerated mechanically. The cultured cells 10 are separated by using the cell dividing member 121.

The present invention, which has been described above, is not limited by the aforementioned exemplary embodiment and the accompanying drawings, and it is obvious to those skilled in the art to which the present invention pertains that various substitutions, modifications and alterations may be made without departing from the technical spirit of the present invention.

The invention claimed is:

1. A method of separating cultured cells, which is used in a configuration comprising:
    a first accommodation space;
    a cell suspension which is present in a liquid in the first accommodation space in a state in which a plurality of cells is connected to one another;
    a filter container having a first end hermetically attached to the first accommodation space, the filter container having a same cross-sectional area as the first accommodation space;
    a cell dividing member mounted within the filter container and having a plurality of through holes having an average diameter of 5 μm to 300 μm; and
    a second accommodation space hermetically attached to a second end of the filter container, the second accommodation space having a same cross-sectional area as the filter container and the first accommodation space;
    wherein the first accommodation space, the filter container and the second accommodation space are horizontally attached in order, allowing an interior of the configuration to have a uniform cross-sectional area;
    wherein one or more of a woven mesh shape, a punched plate shape, and a multi-blade (radiator) shape are used for the cell dividing member;
    wherein the cell suspension horizontally flows from the first accommodation space to the second accommodation space through the filter container in a uniform velocity, the uniform velocity minimizing turbulent flow allowing the cell dividing member to mechanically separated the connection between the cells when the cells collide with the cell dividing member and minimizing damage to the cells.

2. The method of claim 1, wherein the filter container is a sealed container of which the capacity is adjustable.

3. The method of claim 1, wherein the filter container includes a tube through which the cell suspension is moved by being pressed.

4. The method of claim 1, comprising:
a process of moving the cell suspension from the second accommodation space back to the first accommodation space one or more times so as to allow the cell suspension to pass through the cell dividing member several times.

5. The method of claim 4, wherein the filter container is a sealed container of which the capacity is adjustable.

6. The method of claim 4, wherein the filter container includes a tube through which the cell suspension is moved by being pressed.

7. The method of claim 1, wherein a plurality of cell dividing members is formed in the filter container in order to allow the cell suspension to pass through the cell dividing member several times.

8. The method of claim 7, wherein the filter container is a sealed container of which the capacity is adjustable.

9. The method of claim 7, wherein the filter container includes a tube through which the cell suspension is moved by being pressed.

10. The method of claim 1, wherein a second filter container is added to allow the cell suspension to pass through another cell dividing member, and a third accommodation space is formed to be hermetically connected to the second filter container.

11. The method of claim 10, wherein the filter container is a sealed container of which the capacity is adjustable.

12. The method of claim 10, wherein the filter container includes a tube through which the cell suspension is moved by being pressed.

* * * * *